US006500953B1

United States Patent
Mekouar et al.

(12) 
(10) Patent No.: US 6,500,953 B1
(45) Date of Patent: Dec. 31, 2002

(54) PREPARATION OF CAMPTOTHECIN AND NOTHAPODYTINE DERIVATIVES

(75) Inventors: Khalid Mekouar, St. Laurent (CA); Yves Genisson, Toulouse (FR); Stefanie Leue, Chantilly (FR); Andrew-Elliot Greene, Urlange (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/744,547

(22) PCT Filed: May 25, 2000

(86) PCT No.: PCT/FR00/01425

§ 371 (c)(1), (2), (4) Date: Jan. 26, 2001

(87) PCT Pub. No.: WO00/73305

PCT Pub. Date: Dec. 7, 2000

(30) Foreign Application Priority Data

May 28, 1999 (FR) .......................................... 99 06757

(51) Int. Cl.[7] .................... C07D 49/100; C07D 515/00; C09D 498/00
(52) U.S. Cl. .............................. 546/48; 546/62; 546/70
(58) Field of Search ................................ 546/48, 62, 70

(56) References Cited

U.S. PATENT DOCUMENTS

| | | | | |
|---|---|---|---|---|
| 5,247,089 A | * | 9/1993 | Comins et al. ............... | 546/48 |
| 5,475,108 A | * | 12/1995 | Comins et al. ............... | 546/41 |
| 6,211,371 B1 | * | 4/2001 | Curran et al. ................. | 546/48 |
| 6,214,836 B1 | * | 4/2001 | Duvvuri et al. ............. | 514/283 |
| 6,242,457 B1 | * | 6/2001 | Penco et al. ................. | 514/283 |

FOREIGN PATENT DOCUMENTS

| | | | | |
|---|---|---|---|---|
| WO | WO 96/31513 | 10/1996 | ................... | 540/67 |

OTHER PUBLICATIONS

D.L. Boger et al., "Total synthesis of nothapodytine B and (−)–mappicine," *J. Amer. Chem. Soc.*, 120(6): 1218–1222 (1998).

D.L. Comins et al., "Concise synthesis of mappicine ketone and (±)–mappicine," *J. Org. Chem.*, 61(26): 9623–9624 (1996),.

International Search Report for PCT/FR 00/01425, mailed Sep. 12, 2000.

Marco A. Ciufolini and Frank Roschangar, "Practical Total Synthesis of (±)–Camptothecin: The Full Story," *Tetrahedron*, 53(32):11049–60 (1997).

Ei–ichi Negishi et al., "Double Metal Catalysis in the Cross–Coupling Reaction and Its Application to the Stereo–and Regioselective Synthesis of Trisubstituted Olefins," *J. Amer. Chem. Soc.*, 100(7):2254–2256 (1978).

* cited by examiner

*Primary Examiner*—Alan L. Rotman
*Assistant Examiner*—Raymond Covington
(74) *Attorney, Agent, or Firm*—Finnegan, Henderson, Farabow, Garrett & Dunner LLP

(57) ABSTRACT

The invention concerns the preparation of nothapodytine or camptothecin derivatives which consists in causing 4-ethyl 2methyl hepta-2,4-dienoic acid act on a 3-aminomethyl 2-bromo quinoline derivative (III) wherein $R_1$ and $R_2$ are H or $R_1$ is a halogen atom or alkyl, $R_2$ is a O—CO—X radical as defined for the camptothecin derivatives; or $R_1$ and $R_2$ are defined for the known camptothecin derivatives or represent protected radicals or radicals easily convertible into the radicals $R_1$ and $R_2$, to obtain the quinoline derivative (IV); adding to the resulting quinoline derivative (2-methoxy carbonyl vinyl) tributyltin in the presence of a complex of palladium and triphenylarsin to obtain the quinoline derivative (V); cyclizing the resulting quinoline derivative to obtain the tetracyclic derivative (VI); then in subjecting said derivative to an ozonolysis followed by treatment with dimethyl sulphide to obtain the tetracyclic derivative (VII); saponification followed by decarboxylation in oxidising conditions of the resulting tetracyclic derivative to obtain the nothopodytine derivative (VIII); then optionally transforming the resulting derivative into a camptothecin derivative or into a mappicine derivative.

3 Claims, No Drawings

PREPARATION OF CAMPTOTHECIN AND NOTHAPODYTINE DERIVATIVES

This application is a 371 of PCT/FR00/01425 filed May 25, 2000.

The present invention relates to the preparation of camptothecin derivatives. The present invention also relates to the preparation of nothapodytine, mappicine or its derivatives.

In European patent EP 137145, cited here by way of reference, there have been described camptothecin derivatives of general formula:

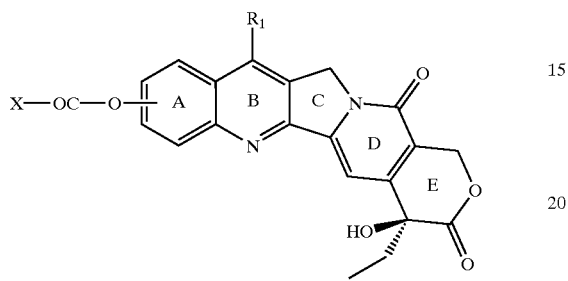

in which in particular $R_1$ is hydrogen, halogen or alkyl, X is a chlorine atom or $NR_2R_3$ for which $R_2$ and $R_3$, which are identical or different, may represent a hydrogen atom, an optionally substituted alkyl radical, an optionally substituted carbocycle or heterocycle, or alkyl derivatives (optionally substituted) forming with the nitrogen atom to which they are attached, a heterocycle optionally containing another heteroatom chosen from O, S and/or $NR_4$, $R_4$ being a hydrogen atom or an alkyl radical and in which the group X—CO—O—is situated at the 9-, 10- or 11-position of the A ring. These camptothecin derivatives are anticancer agents, inhibitors of topoisomerase I, among which irinotecan, for which X—CO—O—is [4-(1-piperidino)-1-piperidino]-carbonyloxy, is an active ingredient which is particularly effective on solid tumors and in particular colorectal cancer.

In patent application EP 74256, cited here by way of reference, there have also been described other camptothecin derivatives which are mentioned as anticancer agents, in particular derivatives having a structure analogous to the structure given above and in which X—CO—O— is replaced by a radical —X'R' for which X' is O or S and R' is a hydrogen atom, an alkyl or acyl radical.

Other camptothecin derivatives have also been described, for example, in patents or patent applications, cited here by way of reference, EP 56692, EP 88642, EP 296612, EP 321122, EP 325247, EP 540099, EP 737686, WO 9003169, WO 9637496, WO 9638146, WO 9638449, WO 9700876, U.S. Pat. No. 7,104,894, JP 57 116015, JP 57 116074, JP 59 005188, JP 60 019790, JP 01 249777, JP 01246287, JP 91 012070 or in Canc. Res., 38 (1997) Abst. 1526 or 95 (San Diego—12–16 April), Canc. Res., 55(3), 603–609 (1995) or AFMC Int. Med. Chem. Symp. (1997) Abst. PB-55 (Seoul—27 July–1 August).

Irinotecan (CPT-11) and its derivatives are usually prepared from natural camptothecin (U.S. Pat. No. 4,604,463; S. SAWADA et al., Chem. Pharm. Bull., 39, 2574–80 (1991), Chem. Pharm. Bull., 39, 1446–54 (1991), Chem. Pharm. Bull., 39, 3183–88 (1991) and Ann. N.Y. Acad. Sci., 803, 13–28 (1996). The steps comprise the introduction of a hydroxyl functional group at the 9-position, and an alkylation at the 11-position and the introduction of the radical at the 9-position.

Mappicine and nothapodytine are known products; nothapodytine is a natural alkaloid possessing an antiviral activity on the HSV-1, HSV-2 and HCMV viruses.

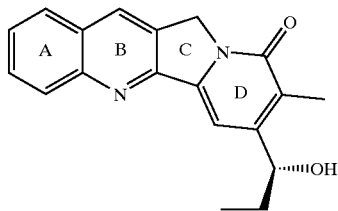

mappicine

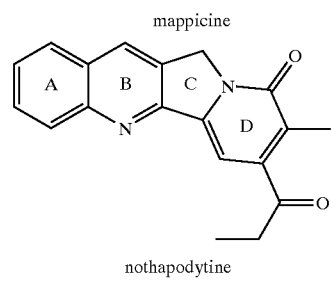

nothapodytine

In international patent application WO 96/31513, there has been described the preparation of camptothecin and mappicine derivatives by total synthesis by preparing, in the first place, the cyclic linkage C-D or C-D-E.

Tetrahedron, 53(32), 11049–60 (1997) also describes the total syntheses of camptothecin derivatives in which the A-B and D-E rings are prepared beforehand, or according to another aspect, the linkages C-D-E or A-B-C.

J. Amer. Chem. Soc., 120, 1218–1222 (1998) and J. Org. Chem., 61, 9623–24 (1996) describe syntheses of nothapodytine from the A-B rings with yields of 17 and 30%, respectively; however, these synthesis routes were not easy to carry out given the preparation of the raw materials involving low temperatures and problems of industrial hygiene.

It has now been found, and it is what constitutes the subject of the present invention, that the camptothecin derivatives, as well as mappicine and nothapodytine, could be obtained by a convergent synthesis from a derivative of 3-aminomethyl-2-bromoquinoline and of 4-ethyl-2-methylhepta-2,4-dienoic acid with particularly advantageous results.

According to the invention, 4-ethyl-2-methyl-hepta-2,4-dienoic acid having the structure:

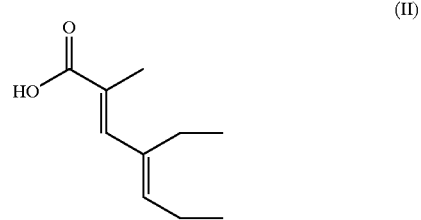

(II)

is condensed with a 3-aminomethyl-2-bromoquinoline derivative of general formula:

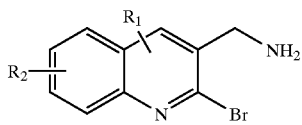

(III)

in which $R_1$ and $R_2$ may be hydrogen atoms or $R_1$ represents a halogen atom or an alkyl radical, $R_2$ is a radical having the structure —O—CO—X as cited above or $R_1$ and $R_2$ are as defined in the references cited above or represent radicals which are protected or which can be easily converted to the radicals $R_1$ and $R_2$ cited above, to give the quinoline derivative of general formula:

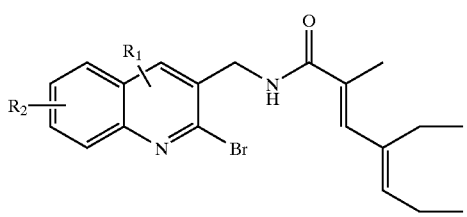

(IV)

in which $R_1$ and $R_2$ are as defined above.

The reaction is generally carried out according to the usual methods for condensing acids with amines, in particular by the action of the acid or of a reactive derivative of the acid.

When the condensation of a reactive derivative of the acid of general formula (II) is carried out, the procedure is advantageously carried out by means of acid chloride, anhydride, a mixed anhydride or a reactive ester in which the ester residue is a succinimido, optionally substituted 1-benzotriazolyl, 4-nitrophenyl, 2,4-dinitrophenyl, pentachlorophenyl or phthalimido.

The reaction is generally carried out at a temperature of between −40 and +40° C., in an organic solvent such as in particular a chlorinated solvent (for example dichloromethane, dichloroethane or chloroform), in the presence of an acid acceptor such as a nitrogen-containing organic base such as for example pyridine, dimethylaminopyridine, N-methylmorpholine or a trialkylamine (in particular triethylamine, diisopropylethylamine) or such as an epoxide (for example propylene oxide). It is also possible to carry out the procedure in the presence of a condensing agent such as a carbodiimide [for example dicyclohexylcarbodiimide or 1-(3-dimethylaminopropyl)-3-ethylcarbodiimide], N,N'-carbonyldiimidazole or 2-ethoxy-1-ethoxycarbonyl-1,2-dihydroquinoline. Preferably, the procedure is carried out under argon or nitrogen.

It is understood that the amino, alkylamino or carboxyl radicals contained in $R_1$ and/or $R_2$ are preferably protected beforehand. In particular, the protection is performed according to the methods described by T. W. Greene and P. G. M. Wuts, Protective Groups in Organic Synthesis (2nd Ed.), A. Wiley-Interscience Publication (1991), or by Mc Omie, Protective Groups in Organic Chemistry, Plenum Press (1973).

(2-Methoxycarbonylvinyl)tributyltin is added to the quinoline derivative of general formula (IV), in the presence of a complex of palladium [such as for example tris (dibenzylidene acetone)dipalladium] and triphenylarsine, to give the quinoline derivative of general formula:

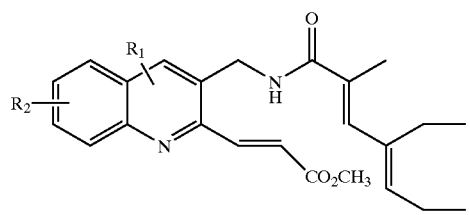

(V)

in which $R_1$ and $R_2$ are as defined above.

The reaction is generally carried out in an organic solvent such as an ether (for example dioxane) at a temperature of between 50 and 110° C. Preferably, the procedure is carried out under argon or nitrogen.

The quinoline derivative of general formula (V), in the presence of triethylamine, is cyclized by addition of t-butyldimethylsilyl triflate to give the tetracyclic derivative of general formula:

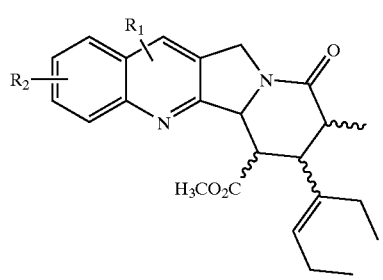

(VI)

in which $R_1$ and $R_2$ are as defined above.

The reaction is carried out in an anhydrous medium, in a chlorinated organic solvent (for example dichloromethane), at a temperature of between −30 and +30° C. Preferably, the procedure is carried out under argon or under nitrogen.

This derivative is subjected to ozonolysis, followed by treatment with dimethyl sulfide to give the ketone derived from the tetracyclic compound of general formula:

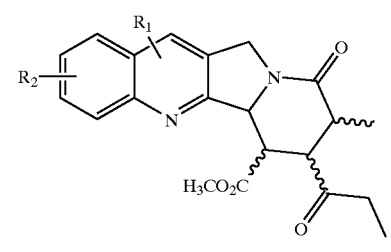

(VII)

in which $R_1$ and $R_2$ are as defined above.

The ozonolysis is carried out in a mixture of chlorinated solvent and alcohol (for example dichloromethane/methanol), at a temperature in the region of −78° C. The product obtained is treated with dimethyl sulfide at a temperature of between −78 and 20° C.

The tetracyclic derivative of general formula (VII) is saponified and then decarboxylated under oxidizing conditions to give the nothapodytine derivative of general formula:

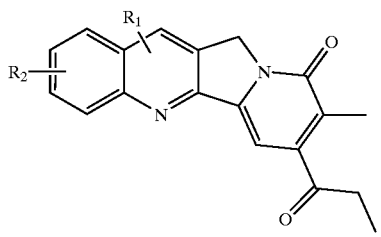

(VIII)

in which $R_1$ and $R_2$ are as defined above.

The reaction is advantageously carried out by treatment with sodium hydroxide in chloromethanolic medium (for example dichloromethane/methanol). The product thus obtained is heated to a temperature of between 130 and 180° C. in the presence of palladium on carbon, in 4-isopropylmethylbenzene. Preferably, the procedure is carried out under argon.

The nothapodytine derivative of general formula (VIII) may be alternatively converted to a mappicine derivative by reducing the ketone functional group by analogy with the method described in J. Am. Chem. Soc., 120, 1218–1222 (1998) or optionally to a camptothecin derivative by conversion, for example, to cyanohydrin and then hydrolysis to a hydroxy ester by analogy with the method described in J. Org. Chem., 51, 5463–5465 (1986), followed by oxidation with the aid of an oxidizing agent such as for example selenium oxide, by analogy with the method described in J. Am. Chem. Soc., 69, 1467 (1947) or J. Heterocycl. Chem., 4, 163 (1967).

The 3-aminomethyl-2-bromoquinoline derivative of general formula (III) in which $R_1$ and $R_2$ are as defined above may be prepared by reducing the corresponding derivative of 3-azidomethyl-2-bromoquinoline of general formula:

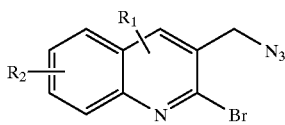

(IX)

in which $R_1$ and $R_2$ are as defined above.

The reduction is carried out by catalytic hydrogenation in the presence of platinum oxide in alcoholic medium (for example ethanol or methanol) at a temperature of between 0 and 30° C.

The 3-azidomethyl-2-bromoquinoline derivative of general formula (IX) is prepared from the 2-bromo-3-bromomethylquinoline derivative of general formula:

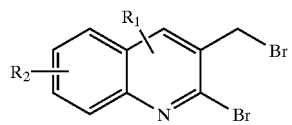

(X)

in which $R_1$ and $R_2$ are as defined above.

The reaction is generally carried out by the action of sodium azide in an organic solvent such as an amide (for example dimethylformamide) at a temperature in the region of 20° C. Preferably, the procedure is carried out under argon or under nitrogen.

4-Ethyl-2-methylhepta-2,4-dienoic acid of general formula (II) may be prepared by hydrolysis or saponification of the corresponding ester as described below in the example.

The methyl ester of 4-ethyl-2-methylhepta-2,4-dienoic acid may be obtained according to the method described by Ei-Ichi Negishi et al., J. Amer. Chem. Soc., 100(7), 2254–2256 (1978).

The products obtained according to the method of the invention may be purified according to the customary techniques used by persons skilled in the art. For example, by chromatography.

The following example, given without limitation, illustrates the present invention.

EXAMPLE 90 mg (0.0007 mol) of dimethylaminopyridine, and then 1.04 g (0.0050 mol) of dicyclohexylcarbodiimide, are added, under argon, to a solution of 1.08 g (0.0046 mol) of 2-aminomethyl-1-bromoquinoline in suspension in 22 ml of $CH_2Cl_2$ at 5° C.

0.850 g (0.0051 mol) of 4-ethyl-2-methyl-hepta-2,4-dienoic acid previously obtained, dissolved in 6 ml of $CH_2Cl_2$, is then added. The stirring is maintained for 60 hours at room temperature, the mixture is then diluted with 20 ml of ethyl ether, and the precipitate thus formed is filtered on 3 cm of celite.

The solvent is evaporated off under reduced pressure (2.7 kPa), the residue thus obtained is purified on a silica column (4% $CH_2Cl_2$/ether) to give 1.57 g of (E,E)-N-(2-bromoquinolin-3-ylmethyl)-4-ethyl-2-methyl-2,4-heptadienamide (yield: 89%).

IR (film, cm–1) ν: 3363, 2971, 2938, 1656, 1564, 1504.

$^1$H NMR (CDCl$_3$, 200 MHz) δ: 8.18 (s, 1H); 7.99 (d, 1H, J=8.6 Hz); 7.80 (d, 1H, J=7.8 Hz); 7.69 (ddd, 1H, J=8.4/7.0/1.7 Hz); 7.54 (ddd, 1H, J=8.0/7.0/1.4 Hz); 6.78 (sl, 1H); 6.49 (sl, 1H, NH); 5.36 (t, 1H, J=7.6 Hz); 4.68 (2s, 2H); 2.14 (q, 4H, J=7.6 Hz); 1.99 (d, 3H, J=1.7 Hz); 0.98 (t, 3H, J=7.6 Hz); 0.93 (t, 3H, J=7.8 Hz)

$^{13}$C NMR (CDCl$_3$, 50 MHz) δ: 169.7; 147.5; 143.1; 138.1; 137.9; 136.9; 134.3; 131.5; 130.3; 129.0; 128.1; 127.7; 127.3; 127.3; 43.4; 23.4; 21.1; 14.2; 14.1; 13.4.

120 mg (0.00013 mol) of tris(dibenzylidenacetone) dipalladium are added, under argon and at room temperature, to a solution of 1.47 g (0.0038) of (E,E)-N-(2-bromoquinolin-3-ylmethyl)-4-ethyl-2-methyl-2,4-heptadienamide dissolved in 59 ml of dry dioxane; the reaction mixture is stirred for 15 minutes, before adding 162 mg (0.0005 mol) of triphenylarsine.

The mixture rapidly loses its color, after stirring for 30 minutes, 2.28 g (0.0061 mol) of (E)-(2-methoxycarbonylvinyl)tributyltin, dissolved in 10 ml of dioxane, are added followed by a few crystals of 2,6-di-tert-butyl-4-methylphenol (BHT).

The reaction mixture is then heated at 80° C. for 7 hours, it is then brought to room temperature and treated with a few drops of a solution of $H_2O$/KF (2/1).

After stirring for 10 minutes, the mixture is taken up in 25 ml of $H_2O$ and extracted with 3 times 60 ml of $CH_2Cl_2$.

The organic phase is dried over $MgSO_4$, filtered and the solvent is evaporated to dryness under reduced pressure (2.7 kPa). The residue thus obtained is purified on a silica column (gradient: 100% $CH_2Cl_2$; 4%; 7%; 15%; 30% ether/$CH_2Cl_2$) to give 1.10 g of the methyl ester of (E)-3-(3-(((E,E)-4-ethyl-2-methyl-2,4-heptadienamido)methyl)quinolin-2-yl) acrylic acid.

m.p.: 119–121° C. (yield: 74%).

IR (film, cm$^{-1}$) ν: 3371, 3053, 2987, 1716, 1656.

$^1$H NMR (CDCl$_3$, 200 MHz) δ: 8.12 (s, 1H); 8.08–7.96 (m, 1H); 7.77 (d, 1H, J=7.8 Hz); 7.69 (t, 1H, J=7.2 Hz); 7.64 (ABq, 2H, δ$_a$=8.03, δ$_b$=7.25, J$_{ab}$=15.2 Hz; 7.51 (t, 1H, J=7.2 Hz); 6.74 (sl, 1H); 6.13 (sl, NH); 5.36 (t, 1H, J=7.6 Hz); 4.79 (2 s, 2H); 3.83 (s, 3H); 2.19–2.06 (m, 4H); 1.98 (s, 3H); 1.02 (t, 3H, J=7.6 Hz); 0.92 (t, 3H, J=7.9 Hz).

¹³C NMR (CDCl₃, 50 MHz) δ: 169.8; 167.0; 151.1; 147.3; 139.1; 137.6; 136.9; 136.3; 134.3; 130.2; 130.0; 129.5; 129.2; 128.1; 127.4; 127.3; 125.0; 51.9; 41.0; 23.4; 21.2; 14.2; 14.1; 13.4.

0.340 g (0.00087 mol) of the methyl ester of (E)-3-(3-(((E,E)-4-ethyl-2-methyl-2,4-heptadienamido)methyl) quinolin-2-yl)acrylic acid is dissolved in 9 ml of dry CH₂Cl₂, before adding, under argon, 0.6 ml (0.0043 mol) of triethylamine.

The reaction mixture is stirred and cooled to 10° C. before adding, under argon, 0.590 ml (0.0026 mol) of t-butyldimethylsilyl triflate.

The stirring is maintained for 3 hours 30 minutes and then the reaction mixture is treated with 8 ml of H₂O and it is extracted with 3 times 10 ml of CH₂Cl₂. The organic phase is dried over MgSO₄, it is then filtered, the solvent is evaporated under reduced pressure (2.7 kPa) and the residue obtained is purified on a silica column (gradient: ether/CH₂Cl₂: 4 to 10%) to give 0.240 g of predominant diastereoisomer, followed by 0.045 g of minor diastereoisomers, that is an overall yield of 84% for the preparation of the methyl ester of 7-(1-ethyl-1-butenyl)-8-methyl-5b,6,7,8-tetrahydro-11H-indolizino[1,2-b]quinolin-9-one-6-carboxylic acid.

For the predominant diastereoisomer:

IR (film, cm–1) ν: 3061, 3053, 2971, 2930, 2873, 1739, 1649, 1576, 1501, 1461, 1436, 1406.

¹H NMR (CDCl₃, 300 MHz) δ: 8.05 (s, 1H); 7.98 (d, 1H, J=8.5 Hz); 7.79 (d, 1H, J=8.0 Hz); 7.66 (ddd, 1H, J=8.5/6.9/1.5 Hz); 7.52 (ddd, 1H, J=8.1/7.0/1.3 Hz); 5.22–5.08 (m, 2H); 4.93 (ABq, 2H, δₐ=5.12, δᵦ=4.73, Jₐᵦ=16.4 Hz); 3.88 (s, 3H); 3.16–2.76 (m, 3H); 2.10–1.73 (m, 4H); 1.10 (d, 3H, J=7.2 Hz); 0.93 (t, 3H, J=7.0 Hz); 0.90 (t, 3H, J=7.6 Hz)

¹³C NMR (CDCl₃, 50 MHz) δ: 173.4; 172.7; 160.5; 149.0; 138.0; 130.7; 130.2; 129.5; 129.3; 127.8; 127.7; 127.6; 126.7; 63.0; 51.9; 49.2; 48.4; 48.1; 38.5; 23.5; 21.0; 14.4; 13.5; 13.5.

In a 50-ml two-necked flask, 0.100 g (0.00025 mol) of the methyl ester of 7-(1-ethyl-1-butenyl)-8-methyl-5b,6,7,8-tetrahydro-11H-indolizino[1,2-b]quinolin-9-one-6-carboxylic acid (predominant diastereoisomer) is dissolved, under argon, in a mixture of 12 ml of CH₂Cl₂ and 2 ml of MeOH.

The reaction mixture is cooled to –78° C. and the argon stream is replaced by an oxygen stream. The ozonolysis apparatus is connected, for twice 90 seconds, and then the excess ozone is purged with oxygen for 15 minutes. 2 ml of dimethyl sulfide are added at –78° C., allowing the temperature to rise gradually to 20° C. overnight.

The solvent is evaporated to dryness, the residue thus obtained is taken up in 10 ml of H₂O, and extracted with CH₂Cl₂. The organic phase is dried and then filtered, the solvent is evaporated off under reduced pressure (2.7 kPa) and the residue thus obtained is purified on a silica column (15% ether/CH₂Cl₂) to give 56 mg of the methyl ester of 8-methyl-7-propionyl-5b,6,7,8-tetrahydro-11H-indolizino[1,2-b]quinolin-9-one-6-carboxylic acid.

m.p. 178–181° C., that is 60% yield.

IR (film, cm⁻¹) ν: 2922, 2848, 1730, 1657.

¹H NMR (CDCl₃, 200 MHz) δ: 8.04 (s, 1H); 7.96 (d, 1H, J=8.2 Hz); 7.79 (dd, 1H, J=8.1/1.4 Hz); 7.66 (ddd, 1H, J=8.4/6.8/1.4 Hz); 7.52 (ddd, 1H, J=8.1/6.8/1.4 Hz); 5.3–5.08 (m, 2H); 4.93 (ABq, 2H, δₐ=5.15, δᵦ=4.72, Jₐᵦ=15.9 Hz); 3.90 (s, 3H); 3.60–3.44 (m, 1H); 3.10–2.92 (m, 1H); 2.47 (qd, 2H, J=7.2/1.4 Hz); 1.16 (d, 3H, J=7.2 Hz); 1.01 (t, 3H, J=7.2 Hz).

¹³C NMR (CDCl₃, 50 MHz) δ: 209.5; 173.1; 170.5; 160.0; 149.1; 130.2; 129.5; 129.4; 127.8; 127.6; 127.5; 126.8; 62.2; 53.5; 52.4; 48.6; 45.3; 37.1; 36.1; 13.8; 7.3.

0.47 ml of a 2 N solution of NaOH is added to 0.100 g (0.00027 mol) of a keto ester solution in 4 ml of CH₂Cl₂, followed by 0.9 ml of MeOH.

The reaction mixture is stirred for 65 hours at room temperature, it is then diluted with 8 ml of H₂O, and then acidified to pH=2–2.5 with a concentrated HCl solution, and extracted with CH₂Cl₂. The organic phase is dried, then filtered and the solvent is evaporated off under reduced pressure (2.7 kPa).

The crude product thus obtained is suspended in 4 ml of 4-isopropylmethylbenzene, 75 mg of 10% Pd/C are then added, under argon, and the reaction mixture is heated under reflux for 1 hour 30 minutes.

After cooling, the mixture is purified directly on a short silica column (100% CH₂Cl₂; 2% MeOH/CH₂Cl₂) to give 0.071 g of the desired product which is washed at cold temperature with twice 1 ml of ice-cold MeOH to give 0.050 g of 8-methyl-7-propionyl-11H-indolizino[1,2-b]quinolin-9-one (nothapodytine).

m.p.: 236–237° C., that is an overall yield of 60%.

IR (KBr, cm⁻¹) ν: 3094; 2988; 2939; 1703; 1651; 1600; 1443; 1378; 1226; 1184; 1143; 932; 838; 762.

¹H NMR (CDCl₃, 300 MHz) δ: 8.34 (s, 1H); 8.17 (d, 1H, J=8.6 Hz); 7.90 (d, 1H, J=7.9 Hz); 7.79 (ddd, 1H, J=8.4/6.9/1.6 Hz); 7.62 (ddd, 1H, J 8.1/6.8/1.2 Hz); 7.23 (s, 1H); 5.27 (2s, 2H); 2.89 (q, 2H, J=7.2 Hz); 2.28 (s, 3H); 1.22 (t, 3H, J=7.2 Hz)

¹³C NMR (CDCl₃, 75.5 MHz) δ: 205.5; 161.7; 152.8; 148.8; 148.1; 143.3; 131.0; 130.4; 129.5; 128.5; 128.1; 128.0; 127.7; 127.0; 97.8; 50.2; 36.0; 13.6; 7.7.

3-Azidomethyl-2-bromoquinoline may be prepared in the following manner:

4.0 g (0.062 mol) of sodium azide are added, under argon and at room temperature, to a solution of 3.69 g (0.0123 mol) of 2-bromo-3-bromomethylquinoline dissolved in 65 ml of dry dimethylformamide.

The reaction mixture is then stirred for 17 hours before being taken up in 60 ml of water and extracted with 3 times 80 ml of CH₂Cl₂.

The organic phase is collected, it is then washed with twice 30 ml of H₂O, it is then dried over MgSO₄, filtered, the solvent is evaporated under reduced pressure (2.7 kPa), and the residue thus obtained is purified on a silica column (5=% AcoEt/cyclohexane) to give 2.63 g. m.p.: 54–56° C. (yield: 82%).

IR (nujol, cm–1) ν: 1706, 1461, 1379.

¹H NMR (CDCl₃, 200 MHz) δ: 8.06 (s, 1H); 7.99 (dd, 1H, J=8.2/1.4 Hz); 7.78 (dd, 1H, J=7.9/1.4 Hz); 7.68 (ddd, 1H, J=8.2/7.0/1.4 Hz); 7.55 (ddd, 1H, J=7.9/7.0/1.4 Hz); 4.6 (s, 2H).

¹³C NMR (CDCl₃, 50 MHz) δ: 147.7; 142.2; 136.8; 130.7; 129.4; 128.3; 127.6; 127.5; 127.0; 53.7.

3-Aminomethyl-2-bromoquinoline may be prepared in the following manner:

1.02 g (0.0039 mol) of azide are dissolved in 110 ml of 95% ethanol, the mixture is purged with argon, before adding 30 mg of platinum oxide hydrate.

The argon is purged 3 times with hydrogen and then the mixture is stirred in the presence of hydrogen for 2 hours at 20° C.

The reaction mixture is purged with argon and then filtered on 3 cm of celite. The filtrate is concentrated under reduced pressure (2.7 kPa) to give 0.863 g, that is 94% yield.

IR (KBr, cm–1) ν: 3338; 2922; 1614; 1586; 1556; 1485; 1449; 1391; 1317.

¹H NMR (CDCl₃, 200 MHz) δ: 8.11 (s, 1H); 7.99 (d, 1H, J=8.2 Hz); 7.78 (d, 1H, J=7.9/1.4 Hz); 7.66 (ddd, 1H, J=8.2/7.0/1.4 Hz); 7.53 (ddd, 1H, J=7.9/7.0/1.4 Hz); 4.04 (s, 2H)

¹³C NMR (CDCl₃, 50 MHz) δ: 147.4; 143.5; 136.2; 135.6; 129.9; 128.2; 127.6; 127.4; 127.2; 45.8.

The methyl ester of 4-ethyl-2-methylhepta-2,4-dienoic acid may be obtained according to the method described by Ei-Ichi Negishi, Nobuhisa Okukado, Anthony O. King, David E. Van Horn, Barry I. Spiegel, J. Amer. Chem. Soc., 100(7), 2254–2256 (1978).

A) Preparation of vinyl zirconium:

5.0 g (0.0194 mol) of zirconocene hydrochloride are added, under argon and at room temperature to a solution of 20 ml of tetrahydrofuran, followed by 2.20 ml (0.01936 mol) of 3-hexyne.

The reaction mixture becomes homogeneous and light red after one hour, and the stirring is maintained for an additional 2 hours.

B) 5 mol % of tetrakis(triphenylphosphine)palladium is added, under argon and at room temperature, to a solution of 20 ml of tetrahydrofuran, followed by the dropwise addition of 3.46 g (0.01933 mol) of methyl (E)-2-bromomethacrylate dissolved in 5 ml of tetra-hydrofuran, immediately followed by the addition of 2.60 g (0.0191 mol) of zinc chloride.

After stirring for 24 hours, 50 ml of H₂O are added, the mixture is extracted with 4 times 50 ml of CH₂Cl₂, the organic phase is then dried over MgSO₄ and filtered. After concentration under reduced pressure (2.7 kPa) at a temperature of less than 20° C., the solid thus obtained is extracted with pentane: 3 times 30 ml, the liquid phase is filtered on cotton wool, then the pentane is evaporated off under reduced pressure (2.7 kPa) at a temperature of less than 20° C. and the residue thus-obtained is chromatographed on a silica column (3% AcOEt/Cyclohexane) to give 2.12 g of the desired methyl ester (yield: 61%). Methyl (E)-2-bromomethacrylate prepared according to Bull. Soc. Chim. Fr, No. 3–4, 487–492 (1976).

IR (film, cm⁻¹) ν: 2971, 2938, 2865, 1706, 1632, 1257.

¹H NMR (CDCl₃, 200 MHz) δ: 7.06 (sl, 1H); 5.45 (t, 1H, J=8.0 Hz); 3.72 (s, 3H); 2.23–2.04 (m, 4H); 1.95 (d, 3H, J=,1.4 Hz); 0.99 (t, 3H, J=7.6 Hz); 0.93 (t, 3H, J=7.6 Hz).

¹³C NMR (CDCl₃, 50 MHz) δ: 169.4; 142.0; 137.2; 135.5; 126.0; 51.7; 23.2; 21.2; 14.1; 13.8; 13.4.

4-Ethyl-2-methylhepta-2,4-dienoic acid may be obtained in the following manner:

10.8 ml (0.0108 mol) of a 1N sodium hydroxide solution are added to a solution of 1.58 g (0.0087 mol) of the ester dissolved in 17 ml of MeOH.

The reaction mixture is then heated under reflux for 30 minutes, it is then diluted at room temperature with 20 ml of a saturated NaHCO₃ solution, and then extracted with 10 ml of ethyl ether.

The aqueous phase is acidified to acidic pH with a concentrated HCl solution at 0° C., it is then extracted with 3 times 15 ml of CH₂Cl₂.

The organic phase is dried over MgSO₄, filtered and the solvent evaporated off under reduced pressure (2.7 kpa) at cold temperature to give 1.20 g of the desired acid (yield: 82%).

IR (film, cm⁻¹) ν: 3249, 2963, 2930, 2873, 1678, 1627, 1415.

¹H NMR (CDCl₃, 200 MHz), δ: 10.4 (sl, 1H); 7.2 (sl, 1H); 5.53 (t, 1H, J=7.2 Hz); 2.26–2.06 (m, 4H); 1.94 (d, 3H, J=1.6 Hz); 1.01 (t, 3H, J=7.2 Hz); 0.96 (t, 3H, J=7.8 Hz).

The camptothecin derivatives are usually administered by injection, more particularly by the intravenous route in the form of a sterile solution or of an emulsion. The camptothecin derivatives may also be administered by the oral route, in the form of solid or liquid compositions.

When the camptothecin derivative is administered by the intravenous route, these compositions may also contain adjuvants, in particular wetting, isotonizing, emulsifying, dispersing and stabilizing agents. Irinotecan (CPT-11) is in particular administered in solution in a medium for intravenous injection, at doses of between 175 to 500 mg/m².

What is claimed is:

1. Process for preparing derivatives of nothapodytine or derivatives of mappicine or of camptothecin, wherein a) 4-ethyl-2-methylhepta-2,4-dienoic acid is reacted on a 3-aminomethyl-2-bromoquinoline derivative of general formula:

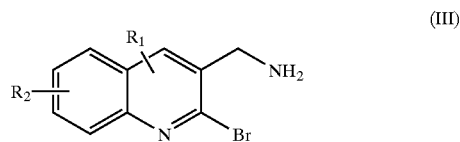

(III)

in which R₁ and R₂ may be hydrogen atoms or R₁ represents a halogen atom or an alkyl radical, R₂ is a radical having the structure —O—CO—X as defined above for the derivatives of camptothecin or R₁ and R₂ are as defined for the known derivatives of camptothecin or represent radicals which are protected or which can be easily converted to the radicals R₁ and R₂ cited above, to give the quinoline derivative of general formula:

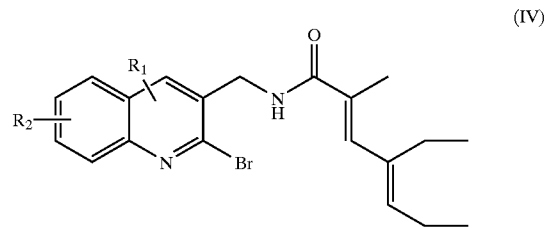

(IV)

in which R₁ and R₂ are as defined above;

b) to the quinoline derivative obtained, (2-methoxycarbonylvinyl)tributyltin is added in the presence of a complex of palladium and triphenylarsine, to give the quinoline derivative of general formula:

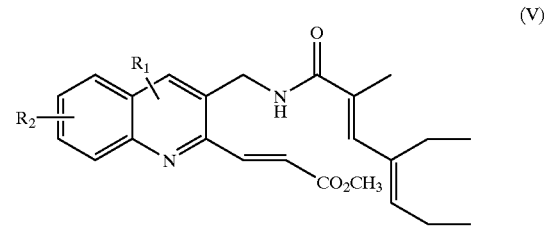

(V)

in which R₁ and R₂ are as defined above;

c) the quinoline derivative obtained is cyclized to give the tetracyclic derivative of general formula:

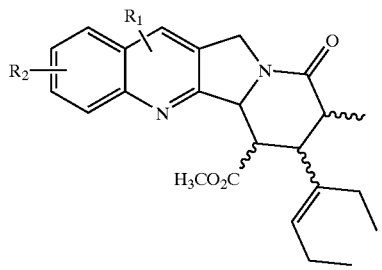

(VI)

in which $R_1$ and $R_2$ are as defined above, then this derivative is subjected to ozonolysis followed by treatment with dimethyl sulfide to give the ketone derived from the tetracyclic compound of general formula:

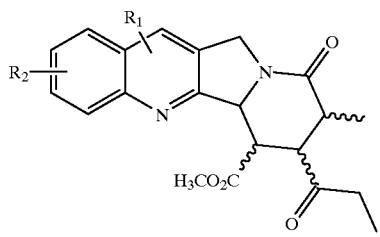

(VII)

in which $R_1$ and $R_2$ are as defined above;

d) the tetracyclic derivative thus obtained is saponified and then decarboxylated under oxidizing conditions to give the nothapodytine derivative of general formula:

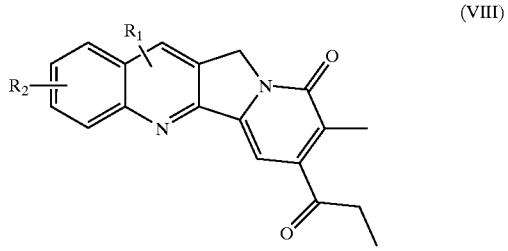

(VIII)

in which $R_1$ and $R_2$ are as defined above, and then the derivative obtained is optionally converted to a camptothecin derivative or to a mappicine derivative.

2. Process according to claim 1, wherein the cyclization step is carried out in the presence of triethylamine and of t-butyldimethylsilyl triflate.

3. Process for preparing nothapodytine or its derivatives, wherein
   a) the compound of formula (V) obtained in step b) of claim 1 is cyclized
   b) then the product obtained in step a) is subjected to ozonolysis followed by treatment with dimethyl sulfide
   c) then the product obtained in step b) is saponified and decarboxylated.

* * * * *